US010089735B2

(12) United States Patent
Nakajima

(10) Patent No.: US 10,089,735 B2
(45) Date of Patent: Oct. 2, 2018

(54) IMAGE PROCESSING METHOD TO DIAGNOSE CUTANEOUS LESION, DIAGNOSTIC APPARATUS USED FOR THE SAME METHOD, AND MEDIUM STORING PROGRAM ASSOCIATED WITH THE SAME METHOD

(71) Applicant: CASIO COMPUTER CO., LTD., Shibuya-ku, Tokyo (JP)

(72) Inventor: Mitsuyasu Nakajima, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 220 days.

(21) Appl. No.: 14/995,031

(22) Filed: Jan. 13, 2016

(65) Prior Publication Data

US 2016/0275675 A1 Sep. 22, 2016

(30) Foreign Application Priority Data

Mar. 18, 2015 (JP) ................................ 2015-054328

(51) Int. Cl.
*G06T 7/00* (2017.01)
*G06T 5/00* (2006.01)
(Continued)

(52) U.S. Cl.
CPC ............ *G06T 7/0012* (2013.01); *A61B 5/444* (2013.01); *G06T 5/002* (2013.01); *G06T 5/20* (2013.01);
(Continued)

(58) Field of Classification Search
CPC ................................ A61B 5/444; G06T 5/20
See application file for complete search history.

(56) References Cited

U.S. PATENT DOCUMENTS 6,760,401 B2 7/2004 Schmitz et al.
9,495,582 B2 11/2016 Gulssin et al.
(Continued)

FOREIGN PATENT DOCUMENTS

EP 2750101 A1 7/2014
JP 2003158677 A 5/2003
(Continued)

OTHER PUBLICATIONS

Japanese Office Action (and English translation thereof) dated Feb. 21, 2017 issued in counterpart Japanese Application No. 2015-054328.
(Continued)

*Primary Examiner* — Kim Vu
*Assistant Examiner* — Molly Delaney
(74) *Attorney, Agent, or Firm* — Holtz, Holtz & Volek PC

(57) ABSTRACT

The invention provides a method of processing an image in a diagnostic apparatus of diagnosing a cutaneous lesion using a cutaneous image, comprising the steps of: (a) obtaining a first detail image made by performing a first component separation filter on a brightness component of the cutaneous image; (b) obtaining a second detail image made by performing a second component separation filter on the brightness component of the cutaneous image, the second component separation filter having properties different from those of the first component separation filter; (c) generating a third detail image based on the first detail image and the second detail image; (d) newly generating a third base image based on the third detail image; and (e) combining the third detail image with the third base image to restore a brightness component and generate a highlighted image.

13 Claims, 10 Drawing Sheets

(51) Int. Cl.

| | |
|---|---|
| ***G06T 5/20*** | (2006.01) |
| ***A61B 5/00*** | (2006.01) |
| ***G06T 5/50*** | (2006.01) |
| ***G06T 7/11*** | (2017.01) |

(52) U.S. Cl.

CPC .................. *G06T 5/50* (2013.01); *G06T 7/11* (2017.01); *G06T 2207/10024* (2013.01); *G06T 2207/10056* (2013.01); *G06T 2207/20028* (2013.01); *G06T 2207/20192* (2013.01); *G06T 2207/20224* (2013.01); *G06T 2207/30088* (2013.01); *G06T 2207/30096* (2013.01)

(56) References Cited

U.S. PATENT DOCUMENTS

| | | | | |
|---|---|---|---|---|
| 2006/0210132 | A1* | 9/2006 | Christiansen, II ... | A61B 5/0059 382/128 |
| 2008/0275315 | A1 | 11/2008 | Oka et al. | |
| 2012/0327205 | A1* | 12/2012 | Takahashi ................ | A61B 1/04 348/65 |
| 2014/0184916 | A1 | 7/2014 | Steiner et al. | |
| 2014/0328509 | A1 | 11/2014 | Guissin et al. | |

FOREIGN PATENT DOCUMENTS

| | | | |
|---|---|---|---|
| JP | 2005192944 | A | 7/2005 |
| JP | 2015507241 | A | 3/2015 |
| JP | 2016087275 | A | 5/2016 |
| JP | 2016120262 | A | 7/2016 |

OTHER PUBLICATIONS

Extended European Search Report dated Jul. 27, 2016, issued in counterpart European Application No. 16150884.1.

Liu, et al., "Melanin and Hemoglobin Identification for Skin Disease Analysis", 2013 Second IAPR Asian Conference on Pattern Recognition, Nov. 5, 2013, pp. 145-149.

Petrella, et al., "Gabor filter for the segmentation of skin lesions from ultrasonographic images", AIP Conference Proceedings, Jan. 1, 2012, pp. 339-342.

Sultana, et al., "Preliminary Work on Dermatoscopic Lesion Segmentation", 20th European Signal Processing Conference (EUSIPCO), Aug. 27, 2012, pp. 2273-2277.

* cited by examiner guided filter bilateral filter

IMAGE PROCESSING METHOD TO DIAGNOSE CUTANEOUS LESION, DIAGNOSTIC APPARATUS USED FOR THE SAME METHOD, AND MEDIUM STORING PROGRAM ASSOCIATED WITH THE SAME METHOD

CROSS-REFERENCE TO RELATED APPLICATIONS

This application claims priority from Japanese Patent Application No. 2015-054328 filed on Mar. 18, 2015, which is incorporated herein by reference.

TECHNICAL FIELD

The present invention relates to an image processing method to diagnose a cutaneous lesion, a diagnostic apparatus used for the same method, and a medium storing program associated with the same method.

BACKGROUND ART

Generally, visual inspection is necessarily performed to diagnose a cutaneous lesion, thereby obtaining an amount of information. However, not only discrimination between a mole and a spot but also discrimination between a benign tumor and a malignant tumor are substantially difficult with a naked eye inspection and even a magnifying glass inspection. For the reasons, dermoscopic inspection in which a dermoscope-equipped camera is used to capture an image of a disease has been conventionally performed.

The dermascope is a noninvasive diagnostic device in which a disease irradiated with light from, for example, a halogen lamp, and unobstructed by reflective light due to echo gel or a polarization filter is magnified (typically ×10) and subjected to observation. A dermoscopic diagnosis can be defined as the inspection of skin diseases with the dermoscope. For more detail, see "ULTRA SIMPLE GUIDE FOR DERMOSCOPY" authored by Masaru Tanaka, a professor of department of dermatology in Tokyo Women's Medical University Medical Center East, published by Shujunsha on Apr. 1, 2010. In accordance with the dermoscopic diagnosis, scattered reflection occurring due to a cuticle is eliminated, thereby rendering the distribution of pigmentation from an epidermis to a superficial intradermal layer increasingly visible.

For example, Patent Literature 1 (Japanese patent publication No. 2005-192944 (A)) discloses technologies of a remote diagnosis apparatus of diagnosing a pigmented skin disease employing a value such as color, a texture, an asymmetricity, and a circularity based on an image of a skin captured by the dermoscope. In accordance with Patent Literature 1, a portable phone provided with a dermoscope-equipped camera is used, and an image of a skin having a disease of a benign nevus pigmentosus and etc. and having a risk of a melanoma is captured by the dermoscope. The portable phone is connected to an internet due to its network connecting function, and the image of the skin captured is transmitted via the internet to the remote diagnosis apparatus to request a diagnosis. Upon receiving the image of the skin based on the request, the remote diagnosis apparatus uses a melanoma diagnosis program to determine whether based on the image of the skin the disease is a melanoma or not, or in a case where the disease is the melanoma, which stage of the melanoma is. The determination as a result is transmitted to a physician having requested the diagnosis.

CITATION LIST

Patent Literature

[Patent Literature 1] Japanese patent publication No. 2005-192944 (A)

SUMMARY OF INVENTION

In accordance with a first aspect of the invention, there is provided a method of processing an image in a diagnostic apparatus of diagnosing a cutaneous lesion using a cutaneous image, comprising the steps of: (a) obtaining a first detail image made by performing a first component separation filter on a brightness component of the cutaneous image; (b) obtaining a second detail image made by performing a second component separation filter on the brightness component of the cutaneous image, the second component separation filter having properties different from those of the first component separation filter, (c) generating a third detail image based on the first detail image and the second detail image; (d) newly generating a third base image based on the third detail image; and (e) combining the third detail image with the third base image to restore a brightness component and generate a highlighted image.

In accordance with a second another aspect of the invention, there is provided with a diagnostic apparatus of diagnosing a cutaneous lesion using a cutaneous image, comprising a processing unit, the processing unit comprising: a first component separation filter on a brightness component of the cutaneous image to obtain a first detail image; and a second component separation filter on the brightness component of the cutaneous image to obtain a second detail image, the second component separation filter having properties different from those of the first component separation filter, wherein the processing unit generates a third detail image based on the first detail image and the second detail image, newly generates a third base image based on the third detail image, and combines the third detail image with the third base image to restore a brightness component and generate a highlighted image.

In accordance with a third aspect of the invention, there is provided a non-transitory computer readable medium storing a program of processing an image in a diagnostic apparatus of diagnosing a cutaneous lesion using a cutaneous image, the program causing a computer to execute: obtaining a first detail image made by performing a first component separation filter on a brightness component of the cutaneous image; obtaining a second detail image made by performing a second component separation filter on the brightness component of the cutaneous image, the second component separation filter having properties different from those of the first component separation filter, generating a third detail image based on the first detail image and the second detail image; newly generating a third base image based on the third detail image; and combining the third detail image with the third base image to restore a brightness component and generate a highlighted image.

DESCRIPTION OF EMBODIMENTS

Figure 1:
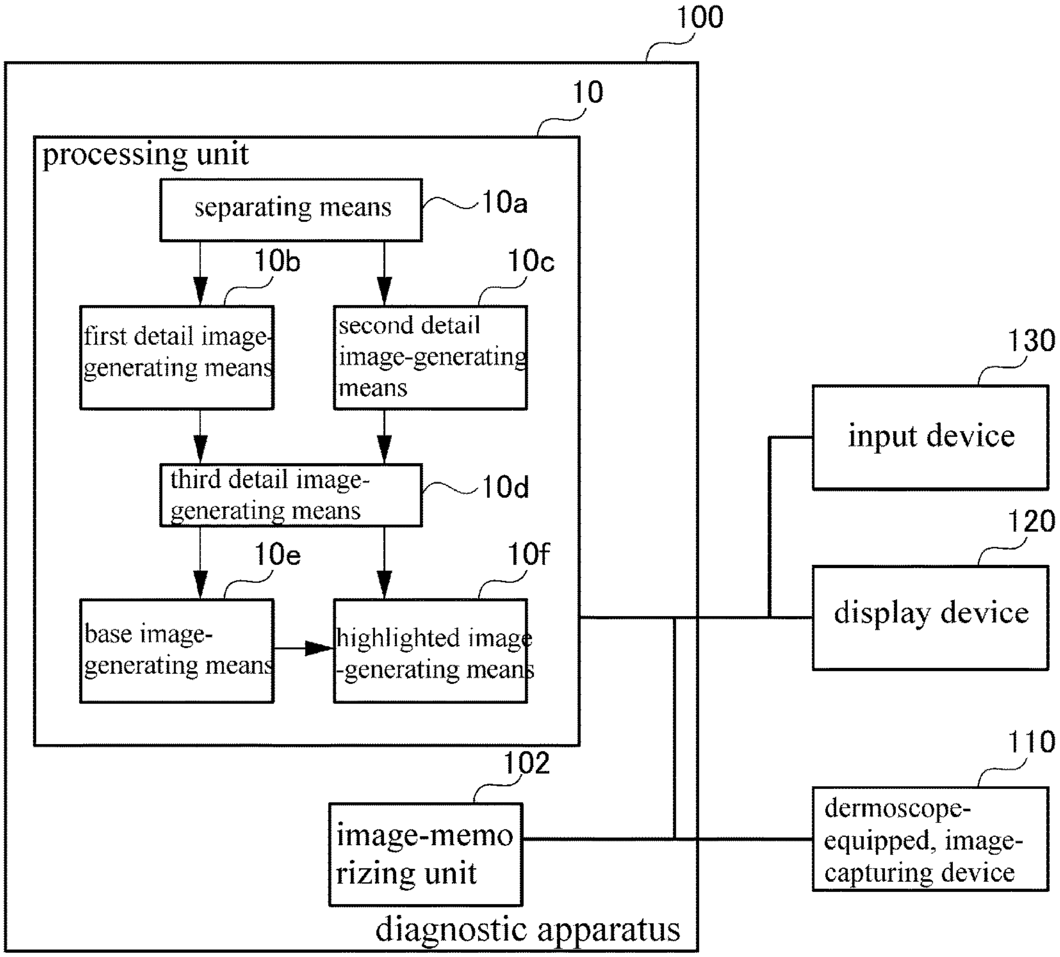
FIG. 1 is a block diagram showing a configuration of one embodiment of a diagnostic apparatus in accordance with the invention.

Referring to the accompanying drawings, an embodiment of the invention will be hereinafter described in detail. Furthermore, the same reference numeral is assigned to the same element or part throughout the overall specification.

[Configuration of Embodiment]

FIG. 1 is a block diagram showing a configuration of a diagnostic apparatus 100, one embodiment of the diagnostic apparatus in accordance with the invention. Referring to FIG. 1, an image-capturing device 110 equipped with a dermoscope, which can be hereinafter designated as an "image-capturing device 110" or "dermoscope-equipped, image-capturing device 110" throughout the specification, is connected to the diagnostic apparatus 100. The dermoscope-equipped, image-capturing device 110 is configured to capture an image in accordance with an instruction from the diagnostic apparatus 100 (in particular, a processing unit 10), memorize the captured image such as a dermoscopic image in an image-memorizing unit 102, and display the captured image on a predetermined area of a display device 120. Furthermore, the captured image is highlighted by the processing unit 101, and then memorized in the image-memorizing unit 102 and displayed on the predetermined area of the display device 120. An input device 130 is configured to perform an instruction for starting to capture an image such as a dermoscopic image, and a selection of a region in the dermoscopic image, which will be described below.

The display device 120 may be a LCD (Liquid Crystal Display) monitor, and the input device 130 may be a mouse.

The processing unit 10 is configured to process the captured image as memorized in the image-memorizing unit 102. Referring to FIG. 1, the processing unit 10 has separating means 10*a*, first detail image-generating means 10*b*, second detail image-generating means 10*c*, base image-generating means 10*d*, and highlighted image-generating means 10*f*.

The separating means 10*a* functions as a means of separating the captured image such as the dermoscopic image into a brightness component and a color information component. In this regard, the separated brightness component and color information component are output at the first detail image-generating means 10*b* and the second detail image-generating means 10*c*.

The first detail image-generating means 101*b* functions as a means of subtracting a first base image, which is obtained by performing a first edge-preserving smooth filter (i.e., a first component separation filter) processing on the brightness component, which is separated by the separating means 10*a*, to attenuate or smooth non-edge area, from the brightness component so as to generate a first detail image, which is output at the third detail image-generating means 10*d*. The second detail image-generating means 10*c* functions as a means of subtracting a second base image, which is obtained by performing a second edge-preserving smooth filter (i.e., a second separation component filter) processing on the brightness component, which is separated by the separating means 10*a*, to attenuate or smooth non-edge area, from the brightness component to generate a second detail image, which is output at the third detail image-generating means 10*d*.

The third detail image-generating means 10*d* functions as a means of generating a third detail image from the first detail image that is output by the first detail image-generating means 1*b* and the second detail image that is output by the second image-generating means 10*c*. The third detail image as generated is output at the base image-generating means 10*e* and the highlighted image-generating means 10*f*. The third detail image-generating means 10*d* generates the third detail image by replacing a plus area of the second detail image with the first detail image. In this regard, the third detail image has been subjected to smoothing processing using, for example, Gaussian filter.

The base image-generating means 10*e* functions as a means of newly generating a third base image using the third detail image that is output by the third detail image-generating means 10*d*. In this regard, the third base image as generated is output at the highlighted image-generating means 10*f*. The third base image is generated by subtracting the third detail image from the brightness component.

The highlighted image-generating means 10*f* functions as a means of combining the third base image that is output by the base image-generating means 10*e* with the third detail image that is output by the third detail image-generating means 10*d*. In more detail, the highlighted image-generating means 10*f* performs coefficient processing and reconstruction to restore the brightness component, and generate a highlighted image using the restored brightness and the color information component that is output by the separating means 10*a*. In this regard, the restored brightness component is reconstructed such that the gain of the third detail image is increased and the gain of the third base image is decreased via the coefficient processing. The highlighted image that is generated by the highlighted image-generating means 10*f* is output at the display device 120.

[Operation of Embodiment]

The operation (i.e., an image processing method) of the diagnostic apparatus 100 as shown in FIG. 1 is hereinafter described in detail with reference to FIG. 2 and below. Furthermore, each of operations or steps which will be hereinafter described can cause a computer to execute a corresponding function using an image processing program in the diagnostic apparatus 100.

Figure 2:
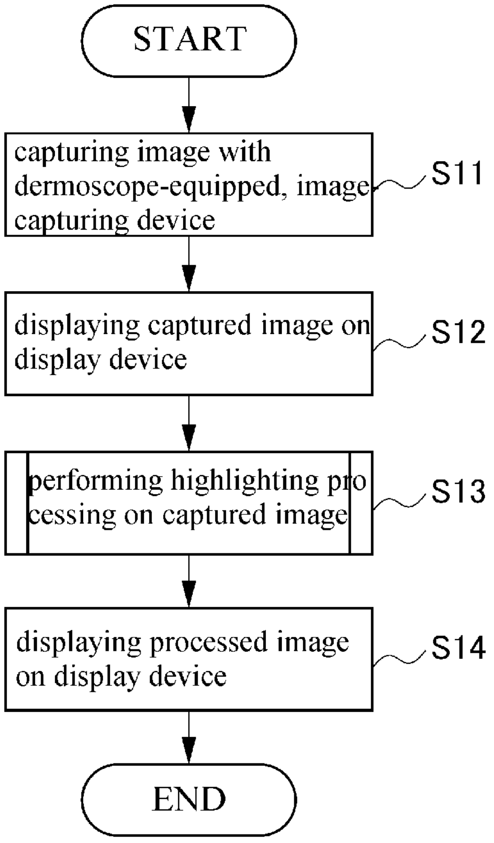
FIG. 2 is a flow chart illustrating a basic processing operation of one embodiment of a diagnostic apparatus in accordance with the invention.

FIG. 2 depicts the flow of basic processing operation of the diagnostic apparatus 100 in accordance with the embodiment of the invention. Referring to FIG. 2, the processing unit 10 firstly acquires an image of an affected area (i.e., a cutaneous lesion) that is captured by the dermoscope-equipped, image-capturing device 110 (Step S11). Then, the captured image as acquired is memorized in the predetermined area of the image-memorizing unit 102, and is displayed on the display device 120 (Step S12). Subsequently, the processing unit 10 performs highlighting processing on the captured image (Step S13), and displays the processed image and the captured image as previously displayed in parallel on the display device 120. Diagnosis is left to a physician (Step S14).

Figure 11:
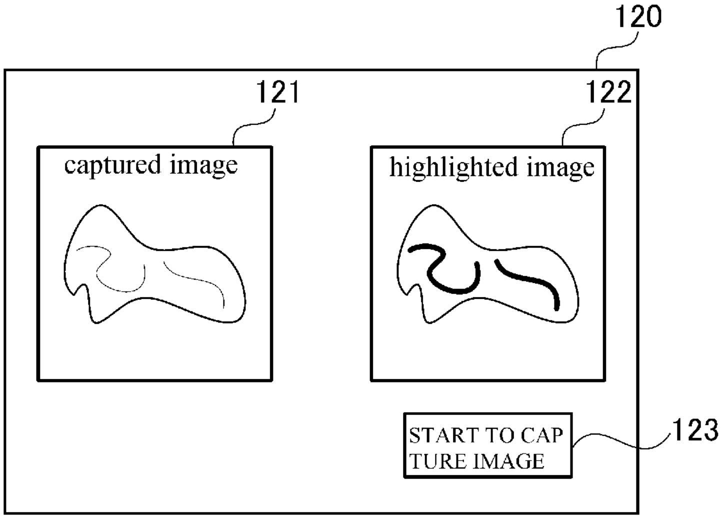
FIG. 11 is an exemplary display screen configuration of an embodiment of a diagnostic apparatus in accordance with the invention.

An exemplary image of a display screen displayed on the display device 120 is shown in FIG. 11. In the screen of FIG. 11, a captured image-displaying section 121 in which the captured image is displayed is arranged at a left side and a highlighted image-displaying section 122 in which the highlighted image of the affected area is shown is arranged at a right side. For example, upon the physician's clicking a button of "start to capture image" 123 which is located at a bottom right of the screen of the display device 120 with the input device 130, the dermoscope-equipped, image-capturing device 110 starts to capture the image of the affected area. Due to the afore-mentioned processing performed by the processing unit 10, the captured image and the highlighted image of the affected area out of the captured image are respectively displayed in the sections 121 and 122 in parallel.

In accordance with the basic concept of the highlighting processing as employed in the embodiment, the resultant image obtained by performing the edge preserving smoothing filter processing on an input image is the base image; the resultant image obtained by subtracting the base image from the input image is the detail image; and the reconstruction is performed such that the gain of the base image is decreased and the gain of the detail image is increased. In this regard, the edge preserving smoothing filter is defined by a filter of performing smoothing while maintaining the edge (i.e., steep gradient). Currently, there is no idealistic edge preserving smoothing filter, and the result of filtering depends on the type of the edge preserving smoothing filter used.

The characteristics of the highlighting modification using the edge preserving smoothing filter is described with reference to FIGS. 3 (*a*) and 3 (*b*). The edge preserving smoothing filter having good filter properties in the non-edge region (i.e., a flat region) is classified into a type that a periphery of the edge region is inclined to be highlighted, and a type that the periphery of the edge region is inclined to attenuate. A filter that ideally processes the periphery of the edge region but cannot process a flat region other than the edge region is not employed in this embodiment. Such a filter may be WS filter (see "Farbman, Fattal, Lischinski, and Detail Manipulation", ACM Transactions on Graphics, 27(3), August 2000). This is because such a filter includes an amount of noise in the detail image to be highlighted. The filter which can successfully perform filtering process on non-edge region is used in the embodiment.

The bilateral filter which is widely used as the edge preserving smoothing filter. Once an associated parameter is set, the bilateral filter operates as shown in, for example, FIG. 3(*b*). The bilateral filter processing is performed on an image L (i.e., the brightness component of the input image) to obtain an image B2 in which the periphery of the edge region is excessively highlighted. In this regard, the detail image is obtained by subtracting the base image from the input image. and represented by "D2". In addition, "D21" is obtained by increasing the gain of D2, and "B21" is obtained by decreasing the gain of B2. D21 is combined with B21 to generate "L21".

In this regard, the parameter of the bilateral filter can be set, as follows: if a pixel of interest is represented by "x"; a value of the pixel of interest is represented by "I(x)"; and an output value of the filter is represented by "γ(x)", the output value of the filter "γ(x)" is defined by: $\gamma(x)=(1/Wp)\Sigma\{I(xi)*f(I(xi)-I(x))*g(xi-x)\}$. In this regard, "Wp" means a normalization term, and is defined by: $Wp=\Sigma\{f(I(xi)-(x))*g(xi-x)\}$. The addition range of Σ is xi that is peripheral pixel of the pixel x. Furthermore, "f ( )" and "g ( )" are defined, as follows:

$$f(j)=\exp(-(j*j)/(2*\sigma r))$$

$$g(j)=\exp(-(j*j)/(2*\sigma s))$$

In the above, "σs" means σ of spatial direction, and "σr" means σ of range (value) direction.

If the brightness of the image L is within a range from 0 to 100, or is preferably around a range from 10 to 30. Furthermore, σs is preferably defined by σs=H/t and t is preferably around a range from 0.001 to 0.02. H is a square root of the number of the total pixels in the image. Alternatively, H is any value between from image width number to image height number. If σs is less than 1, it becomes 1. In other words, the parameters used in a guided filter which will be described below are, as follows:

$$K=\sigma s, eps=\sigma r*\sigma r$$

Figure 3A:
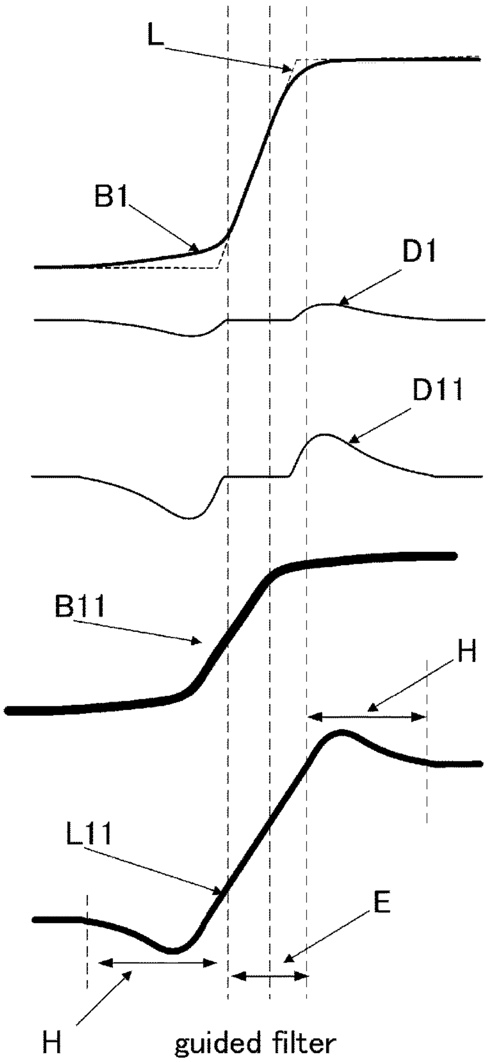
FIGS. 3(*a*) and 3(*b*) illustrate kernel properties of an edge preserving smoothing filter.
Figure 3B:
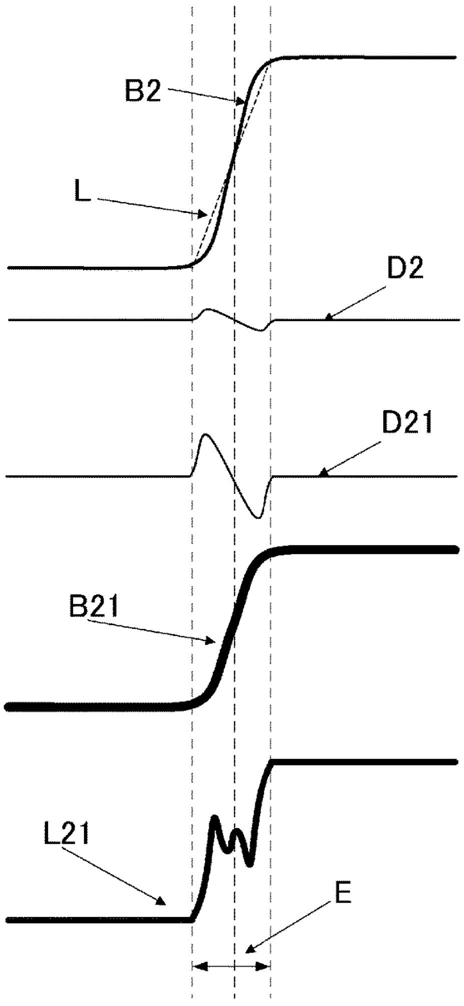

However, in accordance with the bilateral filter, gradient inversion occurs in an edge region E of the modified image L21, as bounded by a dotted line in FIG. 3(*b*). In other words, if the bilateral filter is used, in a case where the gradient of the input signal within the edge region E is great, the gradient inversion occurs in the signal after filtering. The steeper the edge gradient is, the more remarkable the gradient inversion is.

On the other hand, the filter which causes the periphery of the edge region to attenuate (i.e, flatten) includes a guided filter. Given that the input is "I", due to coefficients "A" and "B" the guided filter can be represented by: I'=A*I+B. In this regard, "var ( )" means a variance of neighboring K region, "mean ( )" means an average of the neighboring K region, _a=var (I)/(var (I)+eps), _b=mean (I)−a*mean (I), A=mean (_a), and B=mean (_b).

The space σ (spatial direction) of the bilateral filter corresponds to K, and the range σ (value direction) corresponds to sqrt (eps). FIG. 3(*a*) shows the behavior of the guided filter. Referring to FIG. 3(*a*), the brightness component L of the input image is subjected to the smoothing filter processing using the guided filter so as to obtain B1. Apparently, the periphery of the edge region (i.e., a region bounded by the dotted line) is attenuated. In this regard, the detail image D1 is obtained by subtracting the B1 from the L, and D11 is obtained by increasing the gain of D1. B11 is obtained by decreasing the gain of the B1. The D11 is combined with the B11 to generate L11. According to the L11, there appears an overshoot which is present in a region H outside the edge region E, and is not seen in the input signal L. This is called as "halo", and the periphery of the edge region (i.e., edge neighborhood) blurs. The steeper the edge is, the more remarkable the halo is.

Moreover, the details of the bilateral filter are described in, for example, internet URL (http://en.wikipedia.org/wiki/Bilateral filter), and the details of the guided filter are described in Kaiming He, Jian Sun. Xiaou, Guided Image Filtering. LEEE Transactions on Pattern Analysis and Machine Intelligence, Volume 35, Issue 6, pp. 1397-1409, June 2013.

Figure 4:
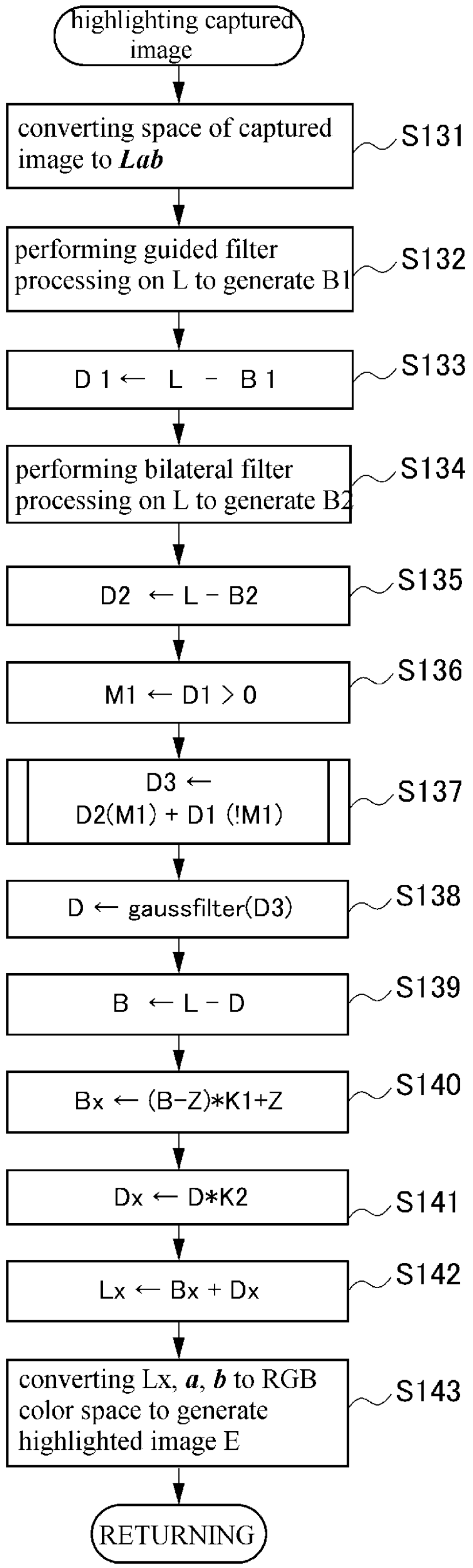
FIG. 4 shows a detailed procedure of "highlighting captured image" as defined in FIG. 2.

FIG. 4 shows a detailed procedure of "highlighting the captured image" as described in Step S13 of FIG. 2. The image-highlighting processing performed by the diagnostic apparatus 100 in accordance with the embodiment as shown in FIG. 1 is hereinafter described in detail with reference to the flow chart of FIG. 4.

The processing unit firstly performs color space conversion. The separating means 10*a* of the processing unit 10 converts the captured image that is obtained by the dermoscope-equipped, image-capturing device 110 from RGB color space to CIE LAB (Lab) color space (more exactly, CIE 1976 L*a*b* color space). The details of the Lab color space are described in, for example, internet URL (http://Ja.wikipedia.org/wiki/lab%E8%89%B2%E7%A9%BA%E9%96%93) (accessed on Mar. 1, 2015).

Figure 5:
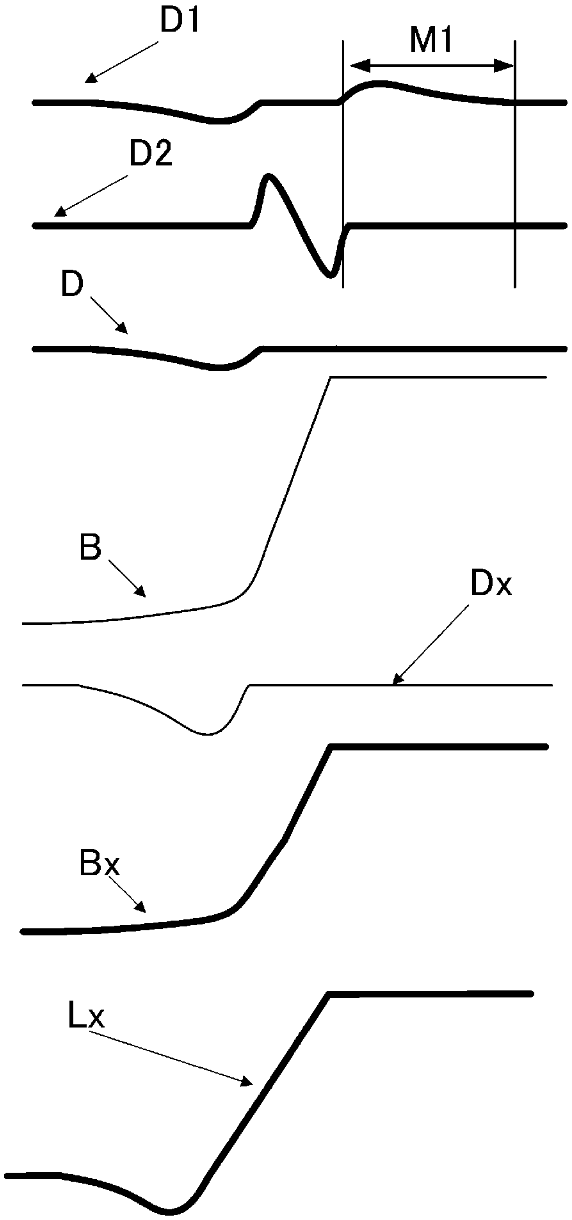
FIG. 5 shows an exemplary brightness signal that is output by an edge preserving smoothing filter.

Next, the first detail image-generating means 10*b* and the second detail image-generating means 10*c* perform the edge preserving smoothing filter processing on the image L, which corresponds to the brightness component of Lab color space and is output by the separating means 10*a*. FIG. 5 shows exemplary signal thereof. In this embodiment, the first detail image-generating means 10*b* performs the guided filter processing on the image L to generate the image B1 (i.e., the first base image)(Step S132), and subtract the image B1 from the image L to generate the D1 (i.e., the first detail image), which is output at the third detail image-generating means 10*d* (Step S133). Furthermore, the second detail image-generating means 10*c* performs the bilateral filter processing on the image L to generate the image B2 (i.e., the second base image) (Step S134), and subtract the image B2 from the image L to generate the image D2 (i.e., the second detail image), which is output at the third detail image-generating means 10*d* (Step S135).

Furthermore, since D1 is a difference between the L and the B1, it has plus and minus signal over the value of "0". The period of time when the signal of D1 is plus is represented by "M1" (Step S136). The third detail image-generating means 10*d* uses the D2 which belongs to the M1 and the D1 which is besides the M1, respectively to generate a new detail image D3 (i.e., a third detail image) (Step S137). To that end, the base image-generating means 10*e* performs Gaussian filter processing on the D3, which is output by the third detail image-generating means 10*d*, to generate the detail image D (Step S138), and subtract the image D from the image L to generate an image B (i.e., a third base image), which is output at the highlighted image-generating means 10*f* (Step S139).

To that end, the highlighted image-generating means 10*f* multiplies the offset value of the image B with Z by K1 to obtain Bx (Step S140). In this regard, "Z" is, for example, an average value of the image B, and "K1" is around a range from 0.3 to 0.8. Furthermore, D is multiplied by K2 to obtain Dx (Step S141). In this regard, "K2" is a value of greater than 1. The highlighted image-generating means 10*f* further adds the Bx to the Dx to generate a modified brightness Lx (i.e., the brightness image after modification) (Step S142). In this regard, since the brightness image in the Lab color space has a value of from 0 to 100, as shown in, for example, FIG. 6, clipping processing is performed such that the value of below 0 becomes 0 and the value of 100 or above becomes 100. The highlighted image-generating means 10*f* finally performs conversion into RGB color space using the modified brightness Lx, a and b of the Lab color space to generate a highlighted image E, which is output at the display device 120 (Step S143).

Furthermore, while the embodiment the Lab color space is used to acquire the brightness image, the Lab color space is not necessarily used. For example, Y in YUV color space or L in HSL space may be used. Alternatively, V in HSV color space may be used. The details of the YUV color space is described in internet URL: https://ja.wikipedia.org/wiki/YUV and the details of the HSV color space is described in internet URL: http://en.wikipedia.org/HSL and HSV.

Figure 6:
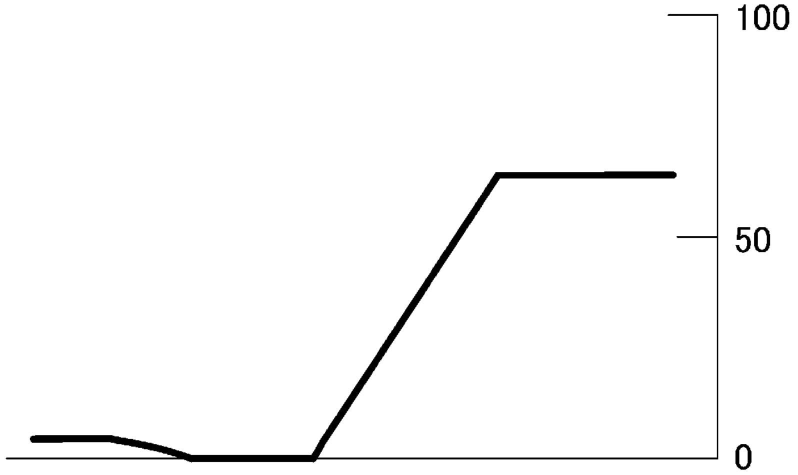
FIG. 6 shows an exemplary brightness signal that is clipped and then outputted.

On the other hand, the properly captured image generally has an intermediate value of the brightness. In other words, the most interested region has the intermediate value. In the modified brightness Lx as shown in FIG. 5, there occurs the halo in a region of low value. In the case of a cutaneous image, the halo may occur in the periphery of black hair and etc. In other words, the halo occurs only when the brightness value of the skin is high, and the brightness value of the hair is particularly low. In the case of general black nevoid, and etc., the halo hardly occurs unless the edge has a particularly steep gradient. Furthermore, if the brightness value is low, the halo becomes less prominent due to the clipping as shown in FIG. 6.

Figure 7A:
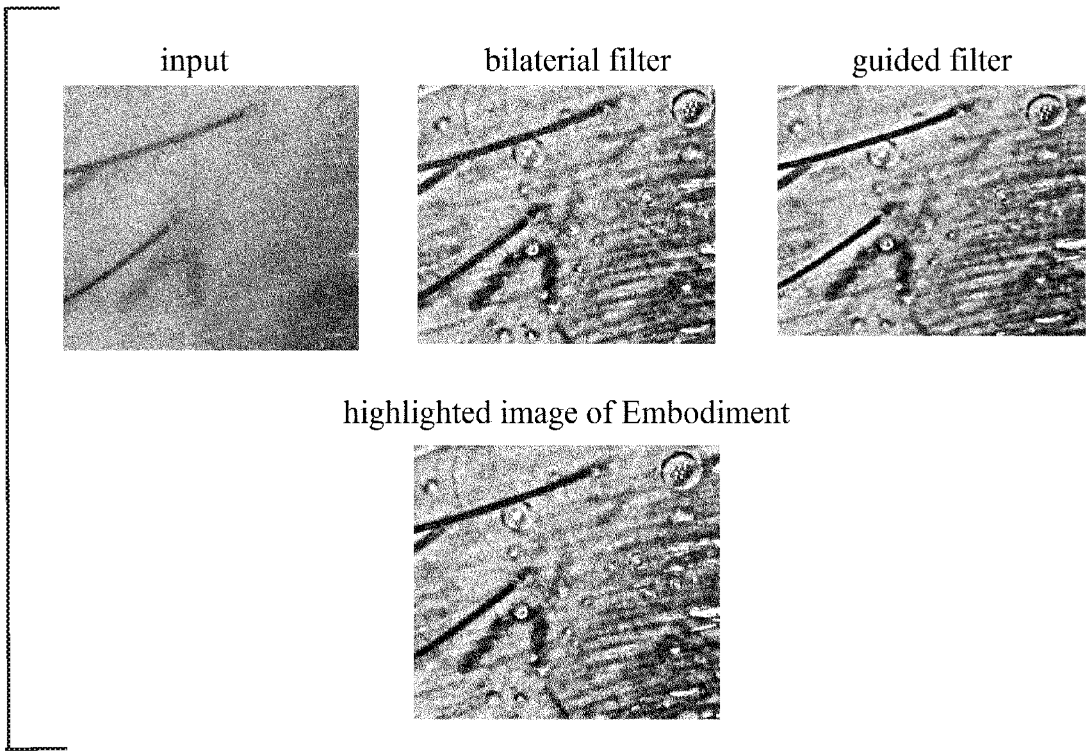
FIGS. 7(*a*) and 7(*b*) show an exemplary highlighted image that is output by a diagnostic apparatus in accordance with an embodiment of the invention in comparison with a conventional example.
Figure 7B:
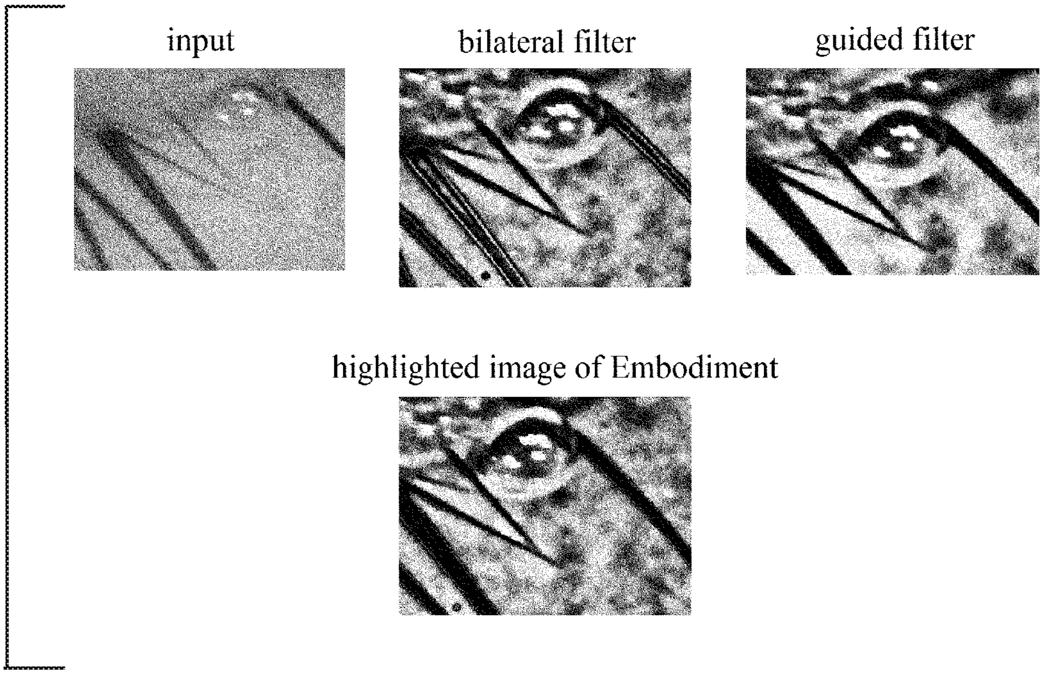

FIGS. 7(*a*) and 7(*b*) show an exemplary highlighted image that is output by a diagnostic apparatus in accordance with an embodiment of the invention in comparison with a conventional example. For example, as shown in FIG. 7(*a*), once performing the bilateral filter processing on the input image, due to the kernel properties of the bilateral filter the edge region of the base image is excessively highlighted, and the gradient inversion occurs in the edge region of the detail image that is obtained by subtracting the base image from the input image. On the other hand, when the guided filter, which does not incur the gradient inversion in the edge region of the detail image and by which the edge region of the base image blurs, is used, moderate gradient inversion (i.e., the halo) occurs in the outer periphery of the edge region. In particular, the steep edge such as a hair, a black nevoid and etc. in the dermoscopic image occurs from the intermediate value to the low value (black side).

In view of the above, the diagnostic apparatus 100 in accordance with the embodiment replaces the guided filter-processed detail image in which the edge region blurs with the detail image, which is generated by the bilateral filter and in which the edge region is highlighted in its plus (+) area. Then, the detail image is subtracted from the input image to obtain the base image, and combined with the base image to provide a highlighted image as represented by "highlighted image of Embodiment" in FIG. 7(*a*). There is not seen any halo or gradient inversion in the highlighted image on the view. Logically, suppressed halo slightly appears in an area of low brightness. Furthermore, since the area of low brightness such as a black hair does not affect the result of diagnosis, wrong diagnosis can be avoided. As such, the output image in which the gradient inversion and halo are suppressed can be generated. The same logic can be applied to an example of FIG. 7(*b*).

[Effect of the Embodiment]

In the afore-mentioned diagnostic apparatus 100 in accordance of the embodiment, the processing unit 10 (1) subtracts the first base image, which is obtained by performing the first component separation filter on the brightness component of the input image, from the brightness component to generate the first detail image; (2) subtracts the second base image, which is obtained by performing the second component separation filter on the brightness component, from the brightness component to generate the second detail image, and generates the third detail image from the first detail image and the second detail image; (3) uses the third detail image to newly generate the third base image; (4) combining the third base image with the third detail image, in more detail via coefficient processing and reconstruction, to restore the brightness component, and uses the restored brightness and the color information component to generate the highlighted image. By adopting the above configuration, the highlighted image in which the gradient inversion, as well as, the halo phenomenon occurring in the steep edge region of the image are suppressed can be displayed, and wrong diagnosis can be thus avoided, thereby enhancing the accuracy of the diagnosis.

Furthermore, in the diagnostic apparatus 100 in accordance with the embodiment, during the highlighting modification of the region where the edge gradient is remarkably great, two highlighting methods performed by the edge preserving smoothing filters can be selectively employed. By adopting the above configuration, the halo only occurs at a suppressed level in an area of low brightness, thereby rendering the method applicable to a wide variety of applications for medical diagnosis other than the dermoscopy.

Application Example 1

Figure 8:
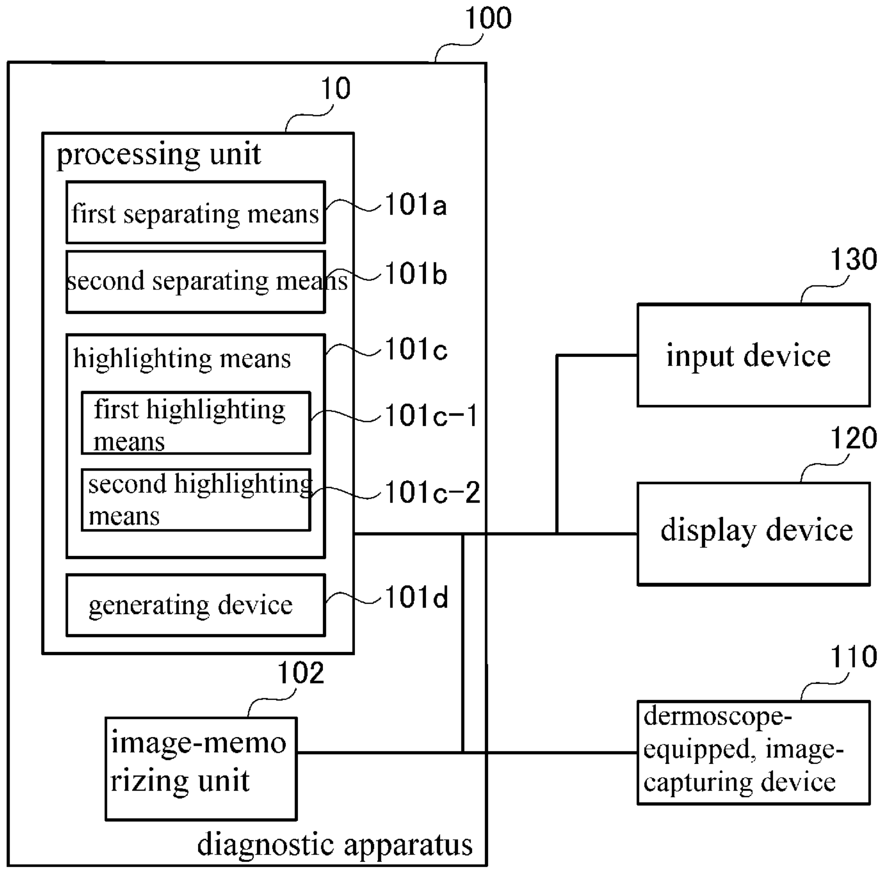
FIG. 8 is a block diagram showing a configuration of Application Example 1 and 2.

FIG. 8 is block diagram showing a configuration of Application Example 1 employing the diagnostic apparatus 100 in accordance of the embodiment. In the afore-mentioned diagnostic apparatus 100, the resultant image that is obtained by performing the edge preserving smoothing filter processing on the input image is the base image; the resultant image that is obtained by subtracting the base image from the input image is the detail image; and the reconstruction is performed such that the gain of the base image is decreased and the gain of the detail image is increased. Due to the above configuration, the image in which the gradient inversion as well as the halo phenomenon occurring in the steep edge region of the image are suppressed can be generated. In the following Application Example 1, the edge preserving smoothing filter processed image is further subject to processing to generate a highlighted image, thereby further improving the accuracy of diagnosis.

Referring to FIG. 8, the processing unit 10 has first separating means 101*a*, second separating means 101*b*, highlighting means 101*c* (first highlighting means 101*c*-1 and second highlighting means 101*c*-2), and generating means 101*d*. The first separating means 101*a* functions as a means of separating the captured image into a brightness component and a color information component. The second separating means 101*b* functions as a means of separating the brightness component into a base component (i.e., a base image) and a detail component (i.e., a detail image). Other devices such as an image-memorizing unit 102, a dermoscope-equipped, image-capturing device 110, a display device 120 and input device 130 are the same as the afore-mentioned embodiment.

The highlighting means 101*c* of the processing unit 10 functions as a means of performing highlighting processing on the base image, and have the first highlighting means 101*c*-which compresses the base image more in a manner brighter than the center value, and/or the second highlighting means 101*c*-2 which performs sharpness filter processing on the base image. The generating means 101*d* functions as a means of restoring brightness from the highlighted base image and the detail image and generating a highlighted image using the color information component.

Furthermore, the first highlighting means 101*c*-1 functions as a means of performing the highlighting processing using a power of a coefficient of 1 or below such that a maximum and a minimum which the base image that is separated by the second separating means 101*b* may have are not changed before and after the highlighting process. Furthermore, the second highlighting means 101*c*-2 functions as a means of generating a compressed image that is obtained by compressing the base image more brightly than the center value and performing a convolution operation of a predetermined convolution coefficient on the compressed image as generated to perform a sharpness filtering process on it.

Each of the first separating means 101*a*, the second separating means 101*b*, the highlighting means 101*c* (the first highlighting means 101*c*-1 and the second highlighting means 101*c*-2), and the generating means 101*d* as described above can execute the afore-mentioned original function thereof by the processing unit 10's sequentially reading a program in accordance with this embodiment of the invention, owned by the processing unit 10.

The image highlighting processing of Application Example 1 as shown in FIG. 8 is hereinafter described in detail with reference to FIGS. 9 and 10. In this regard, the processing unit 10 separates the captured image of the affected area, which is acquired by the dermoscope-equipped, image-capturing device 110, into the base image and the detail image, and performs the highlighting processing on the base image and the detail image in a different manner. The base image and the detail image have undergone the edge preserving smoothing filter processing, which is performed by the diagnostic apparatus 100 in accordance with the embodiment.

Specifically, the processing unit 10 firstly performs color space conversion. The first separating means 101*a* of the processing unit 10 converts the captured image that is obtained by the dermoscope-equipped, image-capturing device 110 from RGB color space to Lab color space (Step S231). Subsequently, the second separating means 101*b* of the processing unit 10 performs the edge preserving filter processing on an image L so as to separate the captured image into the base image and the detail image (Step S232). An edge preserving filter may be a bilateral filter.

Next, the highlighting means 101*c* of the processing unit 10 acquires an image B (B=bilateral filter (L)) that is obtained by performing the bilateral filter processing on the image L. In this regard, the image B is a base image. Next, the highlighting means 101*c* acquires an image D which corresponds to a detail image. The image D can be obtained by subtracting the image B from the image L (Step S233).

Subsequently, the highlighting means 101*c* (in particular, the first highlighting means 101*c*-1) acquires a highlighted base image B1 by raising the base image B to the $p^{th}$ power (Step S234). In this regard, p is 1 or below. The highlighting means 101*c* performs the highlighting processing such that a maximum and a minimum which the base image B may have are not changed before and after modification. Specifically, since the value of the brightness L in the Lab color space is in a range of from 0 to 100, B1 can be determined in accordance with the following mathematical formula: B1=(B^p)/(100^p)*100. Next, the highlighting means 101*c* multiplies B1 by K1 employing the value Z as a basis or standard so as to acquire a compressed image B2 (Step 235).

The compressed image B2 can be determined in accordance with the following mathematical formula: B2=(B1−Z)*K1+Z. In the above mathematical formula, a coefficient "K1" represents a compression ratio of 1 or below, in the embodiment, around a range of from 0.2 to 0.8. Z is set in a manner brighter than a center C. "C" is a center location of value, and can be calculated in accordance with the following mathematical formula: C=(50^p)/(100^p)*100. "Z" has a value of from 5% to 50% greater than that of C.

In other words, the highlighting means 101*c* performs the highlighting processing on the base image by compressing the base image in a manner brighter than the center value.

Next, the highlighting means 101*c* (in particular, the second highlighting means 101*c*-2) performs sharpness filter processing on the compressed image B2 to generate a sharpened image B3 (Step S236: B3←sharpness filter (B2)). During the sharpness filter processing, the second highlighting means 101*c*-2 performs convolution operation of the following kernel M on the compressed image B2. Furthermore, one exemplary convolution matrix (value of convolution kernel M) is shown, as follow:

$$M = \begin{vmatrix} -0.1667 & -0.6667 & -0.1667 \\ -0.6667 & 4.3333 & -0.6667 \\ -0.1667 & -0.6667 & -0.1667 \end{vmatrix}$$

In accordance with the above, the compression highlighting processing is performed by the first highlighting means 101*c*-1, and the subsequent sharpness filter processing is performed by the second highlighting means 101*c*-2. However, the highlighting means 101*c* does not necessarily perform both of the compression highlighting processing and the sharpness filter processing, and may perform either of the compression highlighting processing or the sharpness filter processing.

Next, the highlighting means 101*c* extracts a likelihood of vessel as a likelihood A so as to reflect the likelihood of vessel in a degree of highlighting the detail image D (Step S237). The likelihood of vessel (the likelihood A) has the same dimensional information as the compressed image B2 of the base image in which noise has been removed, and has the likelihood of vessel information (the likelihood A) ranging from 0 to 1 for each pixel. As the likelihood of vessel increases, the value approaches 1. The processing of "extracting the likelihood of vessel as the likelihood A" as defined in Step S237 is illustrated in the flow chart of FIG. 10.

Figure 10:
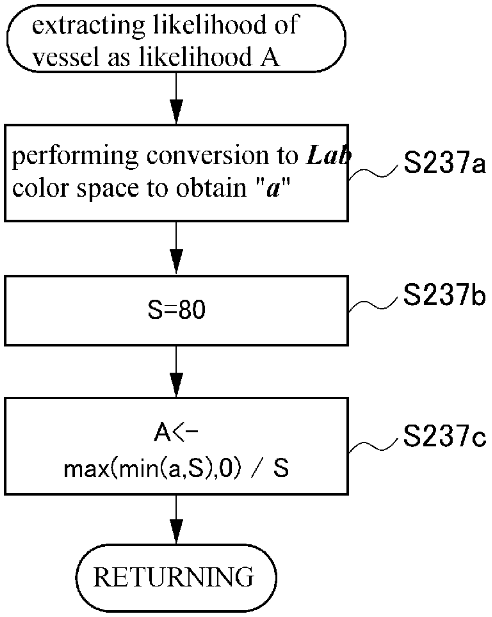
FIG. 10 is a flow chart illustrating a detailed procedure of "extracting likelihood of vessel" as defined in FIG. 9.

Referring to FIG. 10, the highlighting means 101*c* acquires the value of an a axis that corresponds to a direction of red-based color in Lab color space (Step S237*a*), and with respect to the likelihood of vessel (the likelihood A), set the value of the a within the range of from 0 to 1 via normalization with the limited range of from 0 to S (Step S237*b*, Step S237*c*). In this regard, "S" is, for example, 80. In the embodiment, the normalization is performed with limitation of the value of from 0 to 80. However, the above value is only non-restrictive example.

Figure 9:
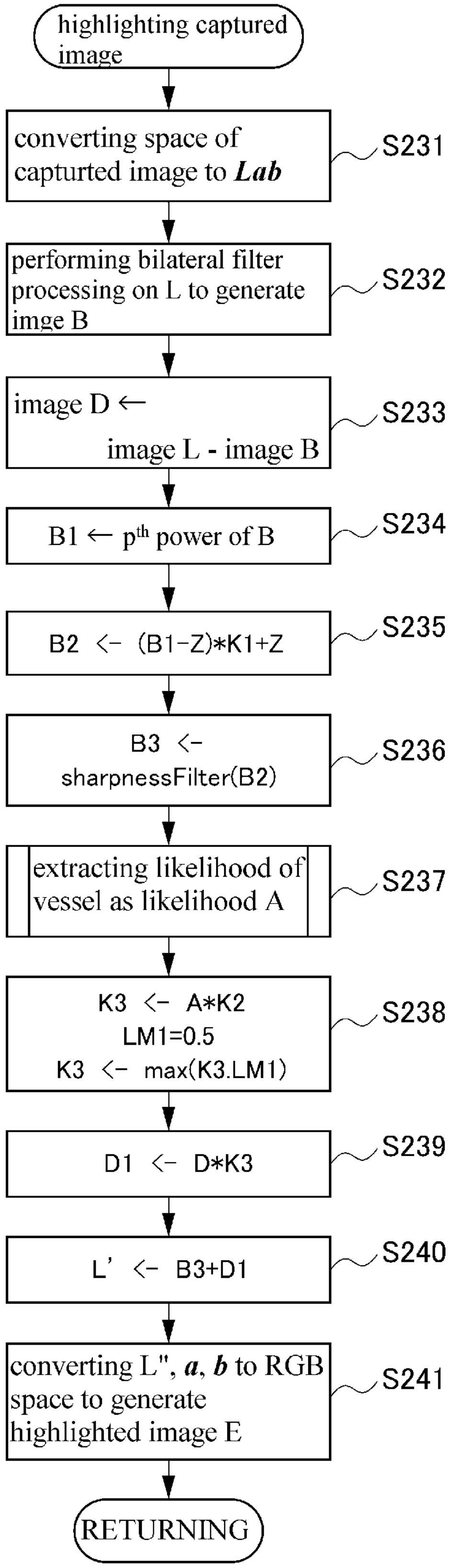
FIG. 9 is a flow chart illustrating a detailed procedure of highlighting processing performed by the diagnostic apparatus of FIG. 8.

Returning to the flow chart of FIG. 9, after determining the likelihood of vessel as the likelihood A as described above (Step S237), the highlighting means 101*c* determines a highlighting coefficient K3 of the detail image D using the likelihood A (Step S238). The highlighting coefficient K3 can be determined in accordance with the following mathematical formula: K3=A*K2. In the above mathematical formula, a lower limit of the highlighting coefficient K3 is obtained by multiplying the coefficient K2 by LM1. In the above mathematical formula, LM1 has a range of from 0 to 1, and may be, for example, 0.5. In other words, K3 can be represented by the following mathematical formula: K3=max (K3, LM1). In the above mathematical formula, "max ( )" is a function returning maximum of two factors per an element. Since "LM1" is a scalar, it is subjected to expansion with the same value and dimension as the highlighting coefficient K3 (Step S169).

Subsequently, the highlighting means 101*c* performs the highlighting processing on the detail image D using the highlighting coefficient K3 to generate the highlighted image D1 of the detail image D (Step S239). In other words, the highlighted image D can be determined in accordance with the following mathematical formula: D1=D*K3. In the above mathematical formula, "*" represents a multiplication per an element.

Subsequently, the generating means 101*d* of the processing unit 10 adds the highlighted (modified) base image B3 to the highlighted (modified) detail image D1 to acquire a modified brightness image L" (L"=B3+D1) (Step S240). Subsequently, based on the modified brightness image L" as acquired, the value of the a axis corresponding to red-based color component and the value of the b axis corresponding to blue-based color component, conversion to the RGB color space is performed to generate an ultimate highlighted image E (Step 241). In other words, the generating means 101*d* restores the brightness from the highlighted base image and detail image, and use the color information component to generate the highlighted image. Furthermore, as shown in the display screen of FIG. 5, the processing unit 10 displays the captured image-displaying section 121 and the highlighted image-displaying section 122 in parallel on the display device 120.

Furthermore, as described above, the highlighting means 101*c* can perform the highlighting processing on either or both of the base image and the detail image. In more detail, the base image is subjected to the highlighting processing via brighter compression or the sharpness filter processing, and the detail image is subjected to the highlighting processing in accordance with the likelihood of vessel. In this regard, the generating means 101*d* does not necessarily require both of the highlighted base image and the highlighted detail image, and may restore the brightness from at least one of the highlighted base image and the highlighted detail image. For example, the generating means 101*d* may add the base image that is highlighted by the highlighting means 101*c* (the image B2 or B3) to the detail image that is separated by the second separating means 101*b* (the image D) to obtain the modified brightness image L".

In accordance with the afore-mentioned Application Example 1, the processing unit 10 separates the captured image as memorized in the image-memorizing unit 102 into the brightness component and the color information component; separates the brightness component into the base image and the detail image; compresses the base image more brightly than the center value or performs the sharpness filtering process on the base image; restores the brightness from the highlighted base image and the detail image; and uses the color information component to generate the highlighted image. As a result, as shown in the display screen of FIG. 11, the processing unit 10 can display the captured image-displaying section 121 and the highlighted image-displaying section 122 in parallel. If the base image is highlighted such that it is compressed more brightly than the center value, the color of the vessel is maintained. If the base image is highlighted via the sharpness filter processing, the base image in the image becomes sharp without being accompanied by any increase in minute noise. For the reasons, the physician can visually check a clear image with respect to, for example, linear vessel or punctate vessel, thereby causing the physician to make an easy and correct diagnosis. As a result, diagnostic accuracy is improved.

In Application Example 1, the bilateral filter is used to separate the brightness component into the base image and the detail image. However, the bilateral filter may be replaced with other edge preserving smoothing filter such as an epsilon filter. Furthermore, while in Application Example 1 the captured image and the highlighted image are displayed in parallel in the captured image-displaying section 121 and the highlighted image-displaying section 122 respectively (FIG. 11), the same effect can be attained by switching and displaying the captured image/the highlighted image on the same screen. Furthermore, while in Application Example 1 the Lab color space is used to acquire the brightness image, a brightness signal Y in YUV color space that is represented by the brightness signal and two color difference signals may be used without use of the Lab color space.

Furthermore, the diagnostic apparatus 100 in accordance with this embodiment uses the a axis of the Lab color space as the likelihood of vessel (likelihood A), it may use an axis that is obtained by rotating the a axis in a plus direction of the b axis about (a1, b1). In this case, a1 is a value of from 10 to 50, b1 is 0, and the amount of rotation is from about 0.3 to 0.8 radian.

Application Example 2

In accordance with the afore-mentioned Application Example 1, the brightness component of the captured image is separated into the base image and the detail image; the base image is compressed more brightly than the center value or is subjected to the sharpness filter processing; and the brightness is restored from the highlighted base image and the detail image; and the highlighted image is generated using the color information component. However, the same effect as Application Example 1 can be obtained by separating the brightness component into the base image and the detail image; performing the highlighting processing on the detail image in accordance with the likelihood of an object to be diagnosed; restoring the brightness from the base image and the highlighted detail image; and generating the highlighted image using the color information component. Application Example 2 is hereinafter described in detail with reference to FIGS. 8-10.

In Application Example 2, a processing unit 10 has first separating means 101*a*, the second separating means 101*b*, highlighting means 101*c*, and generating means 101*d*.

The first separating means 101*a* functions as a means of separating the captured image into a brightness component and a color information component. The second separating means 101*b* functions as a means of separating the brightness component into the base image and the detail image. The highlighting means 101*c* functions as a means of performing highlighting processing on the detail image depending on the likelihood of the region to be diagnosed. In this regard, the highlighting means 101*c* may acquire the color information component that corresponds to a direction of red-based color in a first color space (CIE LAB color space), normalize a predetermined range of the color information component, and reflect a likelihood of the region as acquired via the normalization in a highlighting coefficient of the detail image so as to generate the highlighted detail image.

The generating means 101*d* functions as a means of adding the base image that is separated by the second separating means to the detail image that is highlighted by the highlighting means 101*c* to restore the brightness, and performing a conversion to a second color space (RGB color space) based on the restored brightness and the color information component corresponding to the direction of red-based color and the direction of blue-based color in the first color space (CIE LAB color space) so as to generate the highlighted image.

Each of the first separating means 101*a*, the second separating means 101*b*, the highlighting means 101*c* and the generating means 101*d* as described above can execute the afore-mentioned original function thereof by the processing unit 10's sequentially reading a program in accordance with this embodiment of the present invention, owned by the processing unit 10.

Referring to FIG. 9, the processing unit 10 firstly performs color space conversion. The first separating means 101*a* of the processing unit 10 convert the captured image that is obtained by the dermoscope-equipped, image-capturing device 110 from RGB color space to CIE LAB color space (Step S231). Subsequently, the second separating means 101*b* of the processing unit 10 performs an edge preserving filter processing on an image L to separate the captured image into the base image and the detail image (Step S232). An edge preserving filter which can be used in this edge preserving filter processing may be a bilateral filter.

Next, the highlighting means 101*c* of the processing unit 10 acquires an image B (B=bilateral filter (L)) that is obtained by performing the bilateral filter processing on the image L. In this regard, the image B is a base image. Next, the highlighting means 101*c* acquires an image D which correspond to a detail image. The image D can be obtained by subtracting the image B from the image L (Step S233).

Subsequently, the highlighting means 101*c* (in particular, the first highlighting means) acquires a highlighted base image B11 by raising the base image B to the $p^{th}$ power (Step S234). In this regard, p is 1 or below. The highlighting means 101*c* performs the highlighting processing such that a maximum and a minimum which the base image B may have are not changed before and after modification. Specifically, since the value of the brightness L in the Lab color space is in a range of from 0 to 100, B1 can be determined in accordance with the following mathematical formula: B1=(B^p)/(100^p)*100. Next, the highlighting means 101*c* multiplies B1 by K1 employing the value Z as a basis or standard so as to acquire a compressed image B2 (Step 235).

The compressed image B2 can be determined in accordance with the following mathematical formula: B2=(B1−Z)*K1+Z. In the above mathematical formula, a coefficient "K1" represents a compression ratio of 1 or below, in this example, around a range of from 0.2 to 0.8. Z is set brighter than a center C. "C" is a center location of the value, and can be calculated in accordance with the following mathematical formula: C=(50^p)/(100^p)*100. Z has a value of from 5% to 50% greater than that of C. In other words, the highlighting means 101*c* compresses the base image in a manner brighter than the center value so as to highlight the base image.

Next, the highlighting means 101*c* performs the sharpness filter processing on the compressed image B2 to generate a sharpened image B3 (Step S236: B3←sharpness filter (B2)). During the sharpness filter processing, the highlighting means 101*c* performs convolution operation of kernel M on the compressed image B2, as described previously in connection with Application Example 1.

In Application Example 2, the highlighting means 101*c* performs the compression highlighting processing and the subsequent sharpness filter processing. However, the highlighting means 101*c* does not necessarily perform both of the compression highlighting processing and the sharpness filter processing, and may perform either of the compression highlighting processing or the sharpness filter processing.

Next, the highlighting means 101*c* extracts a likelihood of vessel as a likelihood A so as to reflect the likelihood of vessel in a degree of highlighting the detail image D (Step S237). The likelihood of vessel (the likelihood A) has the same dimensional information as the compressed image B2 of the base image in which noise has been removed, and has the information regarding the likelihood of vessel ranging from 0 to 1 for each pixel. As the likelihood of vessel increases, the value approaches 1.

Referring to FIG. 10, the highlighting means 101*c* acquires the value of an a axis that corresponds to a direction of red-based color in Lab color space (Step S237*a*), and with respect to the likelihood of vessel (the likelihood A), set the value of the a within the range of from 0 to 1 via normalization with the limited range of from 0 to S (Step S237*b*, Step S237*c*). In this regard, S is, for example, 80. In Application Example 2, the normalization is performed with limitation of the value of from 0 to 80. However, the above value is only non-restrictive example.

Returning to FIG. 9, after extracting the likelihood of vessel as the likelihood A as described above (Step S237), the highlighting means 101*c* determines a highlighting coefficient K3 of the detail image D using the likelihood A (Step S238). The highlighting coefficient K3 can be determined in accordance with the following mathematical formula: K3=A*K2. In the above mathematical formula, a lower limit of the highlighting coefficient K3 is obtained by multiplying the coefficient K2 by LM1. In the above mathematical formula, "LM1" has a range of from 0 to 1, and may be, for example, 0.5. In other words, "K3" can be represented by the following mathematical formula: K3=max (K3, LM1). In the above mathematical formula, "max ( )" is a function returning maximum of two factors per an element. Since "LM1" is a scalar, it is subjected to expansion with the same value and dimension as the highlighting coefficient K3. The highlighting means 101*c* performs the highlighting processing on the detail image D using the highlighting coefficient K3 so as to generate the highlighted image D1 of the detail image D (Step S239). In other words, the highlighted image D1 of the detail image can be determined in accordance with the following mathematical formula: D1=D*K3.

Subsequently, the generating means 101*c* of the processing unit 10 adds the highlighted (modified) base image B1 to the highlighted (modified) detail image D1 to acquire a modified brightness image L" (L"=B3+D1) (Step S240). Subsequently, based on the acquired, modified brightness image L", the value of the a axis corresponding to red-based color component and the value of the b axis corresponding to blue-based color component, conversion to the RGB color space is performed to generate an ultimate highlighted image E (Step S241). In other words, the generating means 101*d* restores the brightness from the highlighted base image and detail image, and use the color information component to generate the highlighted image. Furthermore, as shown in the display screen of FIG. 11, the processing unit 10 displays the captured image-displaying section 121 and the highlighted image-displaying section 122 in parallel on the display device 120.

Furthermore, as described above, the highlighting means 101*c* can perform the highlighting processing on the base image and/or the detail image. In more detail, the base image is highlighted via brighter compression or the sharpness filter processing, and the detail image is highlighted in accordance with the likelihood of vessel. In this regard, the generating means 101*d* does not necessarily require both of the highlighted base image and the highlighted detail image, and can restore the brightness from at least one of the highlighted base image and the highlighted detail image. For example, the generating means 101*d* may add the base image that is separated by the second separating means 101*b* (image B) to the detail image that is highlighted by the highlighting means 101*c* (image D1) to obtain the modified brightness image L".

In accordance with above Application Example 2, the processing unit 10 separates the captured image as memorized in the image-memorizing unit 102 into the brightness component and the color information component; separates the brightness component into the base image and the detail image; due to the highlighting means 101*c* performs highlighting processing on the detail image in accordance with the likelihood of region to be diagnosed; and due to the generating means 101*d* restores the brightness from the base image and the highlighted detail image, and uses the color information component to generate the highlighted image. As a result, as shown in the display screen of FIG. 11, the processing unit 10 can display the captured image-displaying section 121 and the highlighted image-displaying section 122 in parallel.

In accordance with Application Example 2, as the detail image is highlighted depending on the likelihood of vessel, the periphery of the vessel becomes sharp without being accompanied by change in overall degree of noise. Accordingly, the physician can visually check the screen that is clear than the captured image with respect to the linear vessel and punctate vessel, thereby causing the physician to make an easy and correct diagnosis. Therefore, diagnostic accuracy is improved. Moreover, the base image is used interchangeably with "base component image", and the detail image is used interchangeably with "detail component image".

The above Embodiment is given to illustrate the scope and spirit of the instant invention. This Embodiment will make apparent, to those skilled in the art, other embodiments and examples. These other embodiments and examples are within the contemplation of the invention. Therefore, the instant invention should be limited only by the appended claims.

100 . . . diagnostic apparatus; 10 . . . processing unit; 10*a* . . . separating means; 10*b* . . . first detail image generating means; 10*c* . . . second detail image-generating means; 10*d* . . . third detail image-generating means; 10*e* . . . base image-generating means; 10*f* . . . highlighted image-generating means; 110 . . . dermoscope-equipped, image-capturing device; 120 . . . display device; 121 . . . captured image-displaying section; 122 . . . highlighted image-displaying section; 130 . . . input device

The invention claimed is:

1. A method of processing an image in a diagnostic apparatus for diagnosing a cutaneous lesion using a cutaneous image, the method comprising:

(a) obtaining a first detail image by performing a first component separation filter processing on a brightness component of the cutaneous image;

(b) obtaining a second detail image by performing a second component separation filter processing on the brightness component of the cutaneous image, the second component separation filter processing having properties different from those of the first component separation filter processing;

(c) generating a third detail image based on the first detail image and the second detail image;

(d) newly generating a third base image based on the third detail image; and (e) combining the third detail image with the third base image to restore a brightness component and generate a highlighted image;

wherein the first component separation filter processing is a first edge preserving smoothing filter processing configured to highlight a periphery of an edge of the cutaneous image, and wherein the second component separation filter processing is a second edge preserving smoothing filter processing configured to attenuate a periphery of an edge of the cutaneous image.

2. The method according to claim 1, wherein in step (e) the highlighted image is generated using a restored brightness component and a color information component.

3. The method according to claim 1, wherein in step (e) the third detail image and the third base image are subjected to a coefficient processing and reconstruction to restore the brightness component and generate the highlighted image.

4. The method according to claim 1, wherein the third base image is generated by subtracting the third detail image from the brightness component.

5. The method according to claim 1, further comprising, prior to step (a), separating the cutaneous image into the brightness component and a color information component.

6. A method of processing an image in a diagnostic apparatus for diagnosing a cutaneous lesion using a cutaneous image, the method comprising:

(a) obtaining a first detail image by performing a first component separation filter processing on a brightness component of the cutaneous image;

(b) obtaining a second detail image by performing a second component separation filter processing on the brightness component of the cutaneous image, the second component separation filter processing having properties different from those of the first component separation filter processing;

(c) generating a third detail image based on the first detail image and the second detail image;

(d) newly generating a third base image based on the third detail image; and (e) combining the third detail image with the third base image to restore a brightness component and generate a highlighted image;

wherein the third detail image is generated by replacing a plus area of the second detail image with the first detail image.

7. The method according to claim 6, wherein the third detail image is subjected to a smoothing filter processing.

8. A method of processing an image in a diagnostic apparatus for diagnosing a cutaneous lesion using a cutaneous image, the method comprising:

(a) obtaining a first detail image by performing a first component separation filter processing on a brightness component of the cutaneous image;

(b) obtaining a second detail image by performing a second component separation filter processing on the brightness component of the cutaneous image, the second component separation filter processing having properties different from those of the first component separation filter processing;

(c) generating a third detail image based on the first detail image and the second detail image;

(d) newly generating a third base image based on the third detail image; and (e) combining the third detail image with the third base image to restore a brightness component and generate a highlighted image;

wherein, in step (a), the first detail image is obtained by subtracting a first base image from the brightness component, the first base image being obtained by performing a first component decomposition filter processing on the brightness component, and wherein, in step (b), the second detail image is obtained by subtracting a second base image from the brightness component, the second base image being obtained by performing a second component decomposition filter processing on the brightness component.

9. The method according to claim 8, wherein the cutaneous image is a dermoscopic image.

10. A method of processing an image in a diagnostic apparatus for diagnosing a cutaneous lesion using a cutaneous image, the method comprising:

(a) obtaining a first detail image by performing a first component separation filter processing on a brightness component of the cutaneous image;

(b) obtaining a second detail image by performing a second component separation filter processing on the brightness component of the cutaneous image, the second component separation filter processing having properties different from those of the first component separation filter processing;

(c) generating a third detail image based on the first detail image and the second detail image;

(d) newly generating a third base image based on the third detail image; and (e) combining the third detail image with the third base image to restore a brightness component and generate a highlighted image;

wherein in step (e) the third detail image and the third base image are subjected to a coefficient processing and reconstruction to restore the brightness component and generate the highlighted image; and wherein, in the coefficient processing, the restored brightness component is reconstructed such that a gain of the third detail image is increased and a gain of the third base image is decreased.

11. A method of processing an image in a diagnostic apparatus for diagnosing a cutaneous lesion using a cutaneous image, the method comprising:

(a) obtaining a first detail image by performing a first component separation filter processing on a brightness component of the cutaneous image;

(b) obtaining a second detail image by performing a second component separation filter processing on the brightness component of the cutaneous image, the second component separation filter processing having properties different from those of the first component separation filter processing;

(c) generating a third detail image based on the first detail image and the second detail image;

(d) newly generating a third base image based on the third detail image; and (e) combining the third detail image with the third base image to restore a brightness component and generate a highlighted image;

wherein the restored brightness component is reconstructed based on the third base image and the third detail image which is highlighted in accordance with a likelihood.

12. A diagnostic apparatus for diagnosing a cutaneous lesion using a cutaneous image, the apparatus comprising:

a processor configured to execute a program stored in a memory to perform operations comprising:

obtaining a first detail image by performing a first component separation filter processing on a brightness component of the cutaneous image;

obtaining a second detail image by performing a second component separation filter processing on the brightness component of the cutaneous image, the second component separation filter processing having properties different from those of the first component separation filter processing;

generating a third detail image based on the first detail image and the second detail image;

newly generating a third base image based on the third detail image; and combining the third detail image with the third base image to restore a brightness component and generate a highlighted image;

wherein the first component separation filter processing is a first edge preserving smoothing filter processing configured to highlight a periphery of an edge of the cutaneous image, and wherein the second component separation filter processing is a second edge preserving smoothing filter processing configured to attenuate a periphery of an edge of the cutaneous image.

13. A non-transitory computer readable medium storing a program for processing an image in a diagnostic apparatus for diagnosing a cutaneous lesion using a cutaneous image, the program causing a computer to execute functions comprising:

obtaining a first detail image by performing a first component separation filter processing on a brightness component of the cutaneous image;

obtaining a second detail image by performing a second component separation filter processing on the brightness component of the cutaneous image, the second component separation filter processing having properties different from those of the first component separation filter processing;

generating a third detail image based on the first detail image and the second detail image;

newly generating a third base image based on the third detail image; and combining the third detail image with the third base image to restore a brightness component and generate a highlighted image;

wherein the first component separation filter processing is a first edge preserving smoothing filter processing configured to highlight a periphery of an edge of the cutaneous image, and wherein the second component separation filter processing is a second edge preserving smoothing filter processing configured to attenuate a periphery of an edge of the cutaneous image.

* * * * *